(12) United States Patent
Doi et al.

(10) Patent No.: US 8,048,842 B2
(45) Date of Patent: *Nov. 1, 2011

(54) THICKENING/FOAM-PROMOTING AGENT

(75) Inventors: Yasuhiro Doi, Wakayama (JP); Masaki Inoue, Wakayama (JP); Kaoru Omae, Wakayama (JP); Yoshinori Tamura, Wakayama (JP)

(73) Assignee: Kao Corporation, Tokyo (JP)

( * ) Notice: Subject to any disclaimer, the term of this patent is extended or adjusted under 35 U.S.C. 154(b) by 344 days.

This patent is subject to a terminal disclaimer.

(21) Appl. No.: 12/090,970

(22) PCT Filed: Oct. 31, 2006

(86) PCT No.: PCT/JP2006/321749
§ 371 (c)(1), (2), (4) Date: Apr. 21, 2008

(87) PCT Pub. No.: WO2007/052657
PCT Pub. Date: May 10, 2007

(65) Prior Publication Data
US 2009/0124523 A1     May 14, 2009

(30) Foreign Application Priority Data

Oct. 31, 2005 (JP) .................. 2005-315652
Jan. 13, 2006 (JP) .................. 2006-006047

(51) Int. Cl.
*C11D 1/722* (2006.01)
*A61K 8/39* (2006.01)
*A61Q 5/02* (2006.01)
*C07C 43/11* (2006.01)

(52) U.S. Cl. ........ 510/421; 510/119; 510/123; 510/128; 510/155; 510/475; 510/490; 424/401; 424/70.11; 424/70.19

(58) Field of Classification Search ............... 510/119, 510/123, 128, 155, 421, 475, 490; 424/401, 424/70.11, 70.19
See application file for complete search history.

(56) References Cited

FOREIGN PATENT DOCUMENTS

| JP | 1 107838 | 4/1989 |
|---|---|---|
| JP | 1 287017 | 11/1989 |
| JP | 6-316782 | 11/1994 |
| JP | 2002-226891 | 8/2002 |
| JP | 2002 308810 | 10/2002 |
| JP | 2002-308810 | * 10/2002 |
| JP | 2003-13092 | 1/2003 |
| JP | 2003-081789 | * 3/2003 |
| JP | 2003-226892 | 8/2003 |
| JP | 2004-98054 | 4/2004 |
| JP | 2004-277685 | 10/2004 |
| JP | 2004 277685 | 10/2004 |

* cited by examiner

*Primary Examiner* — Brian P Mruk
(74) *Attorney, Agent, or Firm* — Oblon, Spivak, McClelland, Maier & Neustadt, L.L.P.

(57) ABSTRACT

The present invention provides a thickening/foam-promoting agent having thickening/foam-promoting properties and a low odor, and a detergent composition containing the agent. The thickening/foam-promoting agent is composed of the following component (A):

(A) a compound represented by the following formula (1):

$$R^1O-(PO)_n/(EO)_m-R^2 \quad (1),$$

wherein $R^1$ is a linear alkyl or an alkenyl group having 8 to 10 carbon atoms, PO is a propyleneoxy group, EO is an ethyleneoxy group, an average added molar number n is a number of 1.5 to 3.0, an average added molar number m is a number of 0 to 1.0, and $R^2$ is a hydrogen atom or a methyl group, wherein the content of an alcohol of the formula (1), when $n=0$, $m=0$ and $R^2$ is a hydrogen atom, is not more than 3000 ppm, and the detergent composition contains the component (A) and a surfactant (B).

11 Claims, No Drawings

THICKENING/FOAM-PROMOTING AGENT

FIELD OF THE INVENTION

The present invention relates to a low-odor thickening/foam-promoting agent composed of propylene oxide and/or ethylene oxide adducts of an alcohol (alkylene glycol ether), i.e., a base material required for a detergent composition having thickening/foam-promoting properties. This invention also relates to a dishwashing composition and a detergent composition which requires rich foaming for the body, such as a shampoo and a body shampoo, with said agent being contained in each of these compositions.

BACKGROUND OF THE INVENTION

It is necessary for a detergent composition to have various functions such as powers to emulsify and solubilize stain components such as an oil, and detergency. A detergent composition for hard surfaces (e.g. a dishwashing agent to be routinely used by humans), a cleansing compositions for the body (e.g., a shampoo or body shampoo) and the like, among others, are required to keep improving the feeling upon use, such as rich foaming, no odor of a base material during use and adequate viscosity, as opposed to other detergents for industrial use. Meanwhile, a less yield of foaming is vital to detergent compositions for industrial use.

In order to enhance a foaming property and adjust a viscosity of a detergent composition, various thickening/foam-promoting agents have been developed, and fatty acid alkanol amides or amides are generally used as a thickening/foam-promoting agents. However, these nitrogen-containing compounds give rise to a change of hue or the like over time, depending on formulation conditions. Furthermore, a fatty acid diethanol amide raises concern about the possibility that its impure nitroso compound might be a cancer-causing substance. For these reasons, a thickening/foam-promoting agent free of nitrogen is desired.

Patent Document 1 discloses, as a thickening/foam-promoting agent free from nitrogen, a (poly)ethyleneglycol alkyl ether obtained by adding 1 to 3 moles of ethylene oxide to an alcohol having 8 to 12 carbon atoms used as a starting material. However, a short chain ethylene oxide adduct containing as few as about 1 to 3 moles of ethylene oxide contains a large amount (not less than 1% by weight) of unreacted alcohols. In addition, alcohols having 8 to 12 carbon atoms carry an strongly unpleasant odor. In particular, if unreacted alcohols having 8 to 10 carbon atoms are left behind in a large amount, the feeling upon use of such a detergent composition could weaken significantly.

While the alcohols may be removed by purification, the production process becomes complicated if the amount of the remaining alcohols is not less than several % by weight, which is industrially unfavorable in view of production cost. On the other hand, it is possible to decrease the amount of unreacted alcohols by increasing the number of ethylene oxide added, but addition of ethylene oxide in a large amount results in poor foaming.

As an example thereof, Patent Document 2 discloses an alkylene oxide adduct of an aliphatic alcohol which is improved in odor by introducing propylene oxide in addition to ethylene oxide. This adduct, however, has a low foaming property when included in a detergent composition, whereby failing to provide a detergent composition having a lower odor and a favorable foaming property.

Patent Document 3 discloses an alkylene oxide adduct of a higher aliphatic alcohol in which a short chain propylene oxide is introduced. However, the document focuses only on the application as an emulsifying agent or a solubilizing agent, and makes no reference to an odor and a foaming property.

Similarly, Patent Document 4 discloses as a detergent an alkylene oxide adduct of an aliphatic alcohol in which a short chain propylene oxide is introduced. However, the document gives no description to an odor and a foaming property.

Patent Documents 5 and 6 disclose a polyoxyalkylene alkyl or alkenyl ether in which a short chain propylene oxide is introduced as a detergent for industrial application. However, these documents make reference only to cleansing of oily matters and iron powder for industrial use, and give no description to an odor and a foaming property. Nor is there any mention about a dishwashing which requires an excellent foaming property, use for the skin or use for the hair.

None of the prior art documents describes the content of a raw material alcohol.

[Patent Document 1] JP-A-2004-277685
[Patent Document 2] JP-A-2003-226892
[Patent Document 3] JP-A-2004-98054
[Patent Document 4] JP-A-2002-226891
[Patent Document 5] JP-A-Hei06-316782
[Patent Document 6] JP-A-2003-13092

DISCLOSURE OF THE INVENTION

The present invention provides a thickening/foam-promoting agent composed of the following component (A):
(A) a compound represented by the following general formula (1):

$$R^1O-(PO)_n/(EO)_m-R^2 \qquad (1)$$

(wherein, $R^1$ represents a linear alkyl or an alkenyl group having 8 to 10 carbon atoms, PO represents a propyleneoxy group, EO represents an ethyleneoxy group, an average added molar number n represents a number of 1.5 to 3.0, an average added molar number m represents a number of 0 to 1.0, and $R^2$ represents a hydrogen atom or a methyl group),
wherein, the content of an alcohol of the formula (1),
wherein n=0, m=0 and $R^2$ is a hydrogen atom, is not more than 3000 ppm.

The present invention also provides a detergent composition containing the following components (A) and (B):
(A) a compound represented by the following general formula (1):

$$R^1O-(PO)_n/(EO)_m-R^2 \qquad (1)$$

(wherein, $R^1$ represents a linear alkyl or an alkenyl group having 8 to 10 carbon atoms, PO represents a propyleneoxy group, EO represents an ethyleneoxy group, an average added molar number n represents a number of 1.5 to 3.0, an average added molar number m represents a number of 0 to 1.0, and $R^2$ represents a hydrogen atom or a methyl group),
wherein, the content of an alcohol of the formula (1),
wherein n=0, m=0 and $R^2$ is a hydrogen atom, is not more than 3000 ppm, and
(B) a surfactant other than component (A).

Further, the present invention provides a process for producing the above-mentioned component (A) in which the content of the raw material alcohol is reduced to not more than 3000 ppm, which comprises reacting a raw material alcohol represented by a general formula (2):

$$R^1OH \qquad (2)$$

(wherein, $R^1$ represents a linear alkyl or an alkenyl group having 8 to 10 carbon atoms) with propylene oxide and/or ethylene oxide, and then distilling away the raw material alcohol.

Furthermore, the present invention provides use of the following component (A) as a thickening/foam-promoting agent.

(A) a compound represented by the following general formula (1):

$$R^1O\text{—}(PO)_n/(EO)_m\text{—}R^2 \tag{1}$$

(wherein, $R^1$ represents a linear alkyl group or an alkenyl group each having 8 to 10 carbon atoms, PO represents a propyleneoxy group, EO represents an ethyleneoxy group, an average added molar number n represents a number of 1.5 to 3.0, an average added molar number m represents a number of 0 to 1.0, and $R^2$ represents a hydrogen atom or a methyl group)
wherein, the content of an alcohol of the formula (1), wherein n=0, m=0 and $R^2$ is a hydrogen atom, is not more than 3000 ppm.

Furthermore, the present invention provides a method for thickening/foam-promoting a detergent composition which comprises using the following component (A):
(A) a compound represented by the following general formula (1):

$$R^1O\text{—}(PO)_n/(EO)_m\text{—}R^2 \tag{1}$$

(wherein, $R^1$ represents a linear alkyl or an alkenyl group having 8 to 10 carbon atoms, PO represents a propyleneoxy group, EO represents an ethyleneoxy group, an average added molar number n represents a number of 1.5 to 3.0, an average added molar number m represents a number of 0 to 1.0, and $R^2$ represents a hydrogen atom or a methyl group)
wherein, the content of an alcohol of the formula (1), wherein n=0, m=0 and $R^2$ is a hydrogen atom, is not more than 3000 ppm.

DETAILED DESCRIPTION OF THE INVENTION

The present invention provides a low-odor thickening/foam-promoting agent and a detergent composition containing said agent, said composition being excellent in foaming property.

According to the present invention, it is possible to obtain a low-odor thickening/foam-promoting agent and a detergent composition having thickening/foam-promoting properties.

In the general formula (1) representing component (A), $R^1$ is a linear alkyl or an alkenyl group having 8 to 10 carbon atoms, and is preferably a linear alkyl group in view of decreasing an odor. In view of foaming property, $R^1$ preferably has 8 carbon atoms, and in the case of a mixture of alkyl groups, it is preferable that not less than 50% by mole, more preferably not less than 80% by mole, even more preferably not less than 98% by mole of the alkyl groups has 8 carbon atoms.

In the general formula (1) representing component (A), PO and EO may be arranged in block or in random order, but are preferably arranged in block. More preferably, in the $(PO)_n/(EO)_m$, $(PO)_n$ and $(EO)_m$ are arranged in block in this order relative to $R^1O$.

In the compounds of the general formula (1) of component (A), the average added molar numbers n and m are restricted in view of meeting a low odor and a foaming property. Namely, if the average added molar numbers n and m are small, the content of the raw material alcohol increases, resulting in increase of an odor. Removal of the raw material alcohol by purification is not favorable in view of production cost. On the other hand, if the average added molar numbers n and m are large, thickening/foam-promoting properties weaken.

The average added molar number n represents a number of 1.5 to 3.0, and is preferably in a range of 2.0 to 3.0, more preferably 2.0 to 2.8, even more preferably 2.3 to 2.8, in view of odor and foaming property. Particularly in view of foaming property, it is preferably in a range of 2.0 to 2.5.

The average added molar number m represents a number of 0 to 1.0, and is preferably 0 in view of foaming property.

A number n+m is preferably in a range of 1.5 to 4.0, more preferably 1.5 to 3.0, even more preferably 2.0 to 2.8, in view of odor and foaming property.

$R^2$ in the general formula (1) represents a hydrogen atom or a methyl group, and is preferably a hydrogen atom.

Component (A) is contained in the detergent composition preferably in an amount of 0.1 to 20% by weight, more preferably 0.3 to 10% by weight, even more preferably 0.5 to 5% by weight, in view of foaming property and economy.

The compounds of formula (1), wherein n=0, m=0 and $R^2$ is a hydrogen atom, are contained in an amount not more than 3000 ppm in view of decreasing an odor, and are preferably not more than 2000 ppm, more preferably not more than 1500 ppm, even more preferably not more than 1000 ppm, far more preferably not more than 500 ppm.

The surfactant of component (B) is one or more surfactants selected from the group consisting of anionic surfactants, nonionic surfactants, amphoteric surfactants and cationic surfactants, and is preferably an anionic surfactant, a nonionic surfactant, or an amphoteric surfactant, particularly preferably an anionic surfactant. Specifically, the following surfactants are illustrated.

The anionic surfactant is preferably a sulphate-based, sulfonate-based, carboxylate-based, phosphate-based or amino acid-based surfactant. Examples thereof include alkyl sulfate salts, polyoxyalkylene alkyl ether sulphate salts, polyoxyalkylene alkenyl ether sulphate salts, sulfosuccinic acid alkyl ester salts, polyoxyalkylene sulfosuccinic acid alkyl ester salts, polyoxyalkylene alkyl phenyl ether sulphate salts, alkane sulfonate salts, acyl isethionates, acyl methyltaurates, salts of higher fatty acids, polyoxyalkylene alkyl ether acetate salts, alkyl phosphate salts, polyoxyalkylene alkyl ether phosphate salts, acyl glutamate salts, alanine derivatives, glycine derivatives, arginine derivatives and the like.

Among these, preferred are polyoxyethylene alkyl ether sulphate salts, polyoxyethylene alkenyl ether sulphate salts, alkyl sulphate salts, salts of higher fatty acids, polyoxyalkylene alkyl ether acetate salts, alkyl phosphate salts, and polyoxyalkylene alkyl ether phosphate salts, and more preferred are those represented by a general formula (3) or (4). Also even more preferred is a phosphoric acid ester-based surfactant which is a mixture of a phosphoric acid monoester represented by a general formula (11) and a phosphoric acid diester represented by a general formula (12), wherein the content ratio by weight satisfies (11)/(12)=100/0-50/50.

$$R^3\text{—}O(CH_2CH_2O)_pSO_3M \tag{3}$$

$$R^4\text{—}OSO_3M \tag{4}$$

(wherein, $R^3$ represents an alkyl or alkenyl group having 10 to 18 carbon atoms, $R^4$ represents an alkyl group having 10 to 18 carbon atoms, M represents an alkali metal, an alkaline earth metal, ammonium, an alkanolamine or a basic amino acid, and p represents an average added molar number of ethylene oxide and is a number of 1 to 5.)

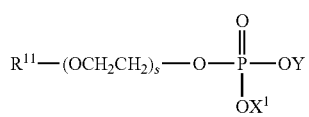

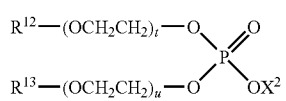

(wherein, $R^{11}$, $R^{12}$ and $R^{13}$ independently represent a linear or branched alkyl or alkenyl group having 8 to 18 carbon atoms, $X^1$, $X^2$ and Y independently represent a hydrogen atom, an alkali metal atom, an alkaline earth metal atom, an alkanolamine or ammonium, and average added molar numbers s, t and u independently represent a number of 0 to 5.)

Examples of the nonionic surfactant include polyoxyalkylene sorbitan fatty acid esters, polyoxyalkylene sorbit fatty acid esters, polyoxyalkylene glycerine fatty acid esters, polyoxyalkylene fatty acid esters, polyoxyalkylene alkyl ethers, polyoxyalkylene alkyl phenyl ethers, polyoxyalkylene (hardened) castor oils, sucrose fatty acid esters, polyglycerine alkyl ethers, polyglycerine fatty acid esters, fatty acid alkanol amides, alkyl glycosides and the like. Among these, preferred are polyoxyalkylene alkyl ethers, alkyl glycosides, polyoxyalkylene C8-C20 fatty acid esters, polyoxyethylene sorbitan fatty acid esters, polyoxyethylene hardened castor oils, and fatty acid alkanol amides, and more preferred are alkyl glycosides and fatty acid alkanol amides. As the polyoxyalkylene alkyl ethers, preferred are polyoxyethylene alkyl ethers, polyoxypropylene alkyl ethers, and polyoxyethylene/polyoxypropylene alkyl ethers. As the alkyl glycosides, preferred are those in which the alkyl group has 8 to 14 carbon atoms and the condensation degree of the sugar (such as glucose) is 1 to 2. As the fatty acid alkanol amides, preferred are those which have an acyl group of 8 to 18 carbon atoms, particularly 10 to 16 carbon atoms, and those having a hydroxyalkyl group of 2 to 3 carbon atoms although they may be either a monoalkanol amide or a dialkanol amide. Examples of the fatty acid alkanol amides include oleic diethanol amide, palm kennel fatty acid diethanol amide, coconut fatty acid diethanol amide, lauric acid diethanol amide, polyoxyethylene coconut fatty acid monoethanol amide, coconut fatty acid monoethanol amide, lauric acid monoisopropanol amide, lauric acid monoethanol amide, palm kennel fatty acid methyl ethanol amide, coconut fatty acid methyl ethanol amide and the like.

Examples of the amphoteric surfactant include betaine-based surfactants and amine oxide-type surfactants. Among these, more preferred are betaine-based surfactants such as imidazoline-based betaines, alkyl dimethylaminoacetic acid betaines, fatty acid amidopropylbetains and sulfobetaines, as well as amine oxide-type surfactants such as alkyl dimethyl amine oxides, and even more preferred are alkylcarboxymethyl hydroxyethyl imidazolium betaines, fatty acid amidopropylbetaines, sulfobetaines such as alkyl hydroxysulfobetaines, alkyl sulfobetaines, fatty acid amidopropyl hydroxylsulfobetaines and fatty acid amidopropyl sulfobetaines, as well as alkyl dimethyl amine oxides. Sulfobetaines such as alkyl hydroxysulfobetaines, alkyl sulfobetaines, fatty acid amidopropyl hydroxylsulfobetaines and fatty acid amidopropyl sulfobetaines are far more preferred in view of the performances that a foaming property is not lost even in the presence of stains, namely in view of a foaming property and a stain resistance, which are required for a detergent composition for dishwashing or body cleansing, as well as in view of thickening property. The alkyl hydroxylsulfobetaines are the most preferred. The fatty acid amidopropylbetaines and the alkyl hydroxylsulfobetaines preferably have an alkyl group of 8 to 18 carbon atoms, particularly 10 to 16 carbon atoms, and particularly lauric acid amidopropylbetaine, palm kennel fatty acid amidopropylbetaine, coconut fatty acid amidopropylbetaine, lauryl hydroxylsulfobetaine, lauryl sulfobetaine, coconut fatty acid amidopropyl hydroxylsulfobetaine, coconut fatty acid amidopropyl sulfobetaines and the like are preferred. Amongst, lauryl hydroxylsulfobetaine is the most preferred. The alkyl dimethyl amine oxides preferably have an alkyl group of 8 to 18 carbon atoms, more preferably 10 to 16 carbon atoms, and lauryl dimethyl amine oxide and myristyl dimethyl amine oxide are most preferred.

Examples of the cationic surfactant include quaternary ammonium salts represented by the following formula (5):

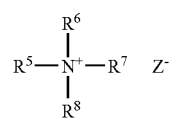

(wherein, at least one of R5, R6, R7 and R8 represents a linear or branched alkyl or alkenyl group having in total 12 to 28 carbon atoms which may be substituted with an alkoxy group, preferably a linear or branched alkoxy group of 16 to 28 carbon atoms, alkenyloxy group, alkanoylamino group, alkenoylamino group, alkanoyl group or alkanoyloxy group, the remainders represent a benzyl group, an alkyl group of 1 to 5 carbon atoms, a hydroxyalkyl group or a polyoxyethylene group having a total added molar number of not more than 10, and $Z^-$ represents a halogen ion or an organic anion such as one selected from acetate, citrate, lactate, glycolate, phosphate, nitrate, sulfonate, sulphate and alkylsulfate groups) as described in JP-A-2000-178146.

Preferred examples of the compound (5) include those in which at least one of $R^5$, $R^6$, $R^7$ and $R^8$ represents an alkyl group having in total 8 to 22 carbon atoms which may be substituted with an alkoxy group, and the remainders represent a methyl group, an ethyl group or a benzyl group. More preferred specific examples include a long-chain monoalkyltrimethyl ammonium chloride such as stearyltrimethyl ammonium chloride or octadecyloxypropyltrimethyl ammonium chloride, a long-chain dialkyldimethyl ammonium chloride such as distearyldimethyl ammonium chloride or a branched dialkyldimethyl ammonium chloride, and the like.

Component (B) is preferably included in the detergent composition in an amount of 3 to 50% by weight, more preferably 5 to 30% by weight, particularly 10 to 30% by weight, in view of foaming property and economy.

The weight ratio of component (A) to component (B) is preferably (A)/(B)=1/200 to 10/1, more preferably 1/100 to 1/1, even more preferably 1/50 to 1/5, most preferably 1/30 to 1/10.

Component (A) is preferably used as a thickening/foam-boosting agent of a detergent composition applied to the skin or the hair.

The thickening/foam-promoting agent and the detergent composition according to the present invention are particularly suitable for application to a body such as the skin or the hair.

The detergent composition according to the present invention may contain an oily component when it is applied particularly to the skin or the hair.

Examples of the oily component include higher alcohols, silicones, ester oils, hydrocarbons, glycerides, vegetable oils, animal oils, lanoline derivatives, higher fatty acid esters and the like, with higher alcohols, ester oils and/or silicones being preferred, and higher alcohols and/or silicones being most preferred.

The detergent composition according to the present invention may optionally contain glycerine, humectants, cationic polymers, polysaccharides, polypeptides, pearlizing agents, solvents, liquid crystal-foaming base materials, dyes, flavours, propellants, chelating agents such as edetate (EDTA) and citrates, pH regulating agents, antiseptics, antidandruff agents and the like. Examples of the cationic polymers include cationized cellulose derivatives, cationic starches, cationized guar gum derivatives and the like. Examples of the antidandruff agents include zinc pyrition, pyrocton olamin and the like.

The pH of the detergent composition of the invention, when diluted to a twenty-fold dilution, is preferably in a range of 3 to 10, more preferably 4 to 9, at 25° C.

In a process for preparing component (A), $R^1$ in the general (2) is a linear chain alkyl or an alkenyl group having 8 to 10 carbon atoms, and is preferably a linear chain alkyl group in view of decreasing an odor. In view of foaming property, $R^1$ is preferably an alkyl group having 8 carbon atoms, and in the case of a mixture of alkyl groups, it contains an alkyl group of 8 carbon atoms in an amount preferably not less than 50% by mole, more preferably not less than 80% by mole, and even more preferably not less than 98% by mole.

In a process for preparing component (A), propylene oxide and ethylene oxide may be added in block or in random order, but are preferably added in block. Further, in view of decreasing an odor, it is preferable to add propylene oxide to a raw material alcohol represented by the general formula (2), and subsequently add ethylene oxide thereto. Addition of only propylene oxide is also preferable. An average added molar number of propylene oxide to a raw material alcohol represented by the general formula (2) is in a range of 1.5 to 3.0 moles, preferably 2.0 to 3.0 moles, more preferably 2.0 to 2.8 moles, even more preferably 2.3 to 2.8 moles, in view of foaming property and decreasing an odor. In view of foaming property, it is preferably 2.0 to 2.5 moles. An average added molar number of ethylene oxide to a raw material alcohol represented by the general formula (2) is in a range of 0 to 1.0 mole, preferably 0 mole in view of foaming property and decreasing an odor. A total average added molar number of propylene oxide and ethylene oxide to a raw material alcohol represented by the general formula (2) is preferably in a range of 1.5 to 4.0 moles, more preferably 1.5 to 3.0 moles, even more preferably 2.0 to 2.8 moles, in view of foaming property and decreasing an odor.

In a process for preparing component (A), the used amount of a basic catalyst is preferably 0.1 to 5% by mole, more preferably 0.1 to 2% by mole of a raw material alcohol represented by the general formula (2).

As to the basic catalyst, there is no particular restriction thereon and known common catalysts may be used. Examples thereof include potassium hydroxide, sodium hydroxide, lithium hydroxide, sodium alkoxides and the like.

The temperature of the reaction between the raw material alcohol and propylene oxide and/or ethylene oxide is 80 to 200° C., preferably 110 to 160° C., more preferably 110 to 130° C., and the reaction pressure is 0.1 to 0.8 MPa, preferably 0.1 to 0.6 MPa.

The reaction product may be subjected to distillation as it is, or may be subjected to distillation after the basic catalyst has been removed by means of a neutralizing agent, an absorbent or the like. No restriction is imposed on the neutralizing agent and the absorbent. Examples of the neutralizing agent include organic acids such as acetic acid and lactic acid, and mineral acids such as phosphoric acid and sulfuric acid (they may be used singly, as a mixture or in combination), and examples of the absorbent include synthetic absorbents such as Kyoword (Kyowa Chemical Industry, Co., Ltd.), activated white clay, activated charcoal, ion exchange resins (they may be used singly, as a mixture or in combination, and also may be used in combination with a neutralizing agent).

The distillation of the raw material alcohol means distilling off the raw material alcohol by distillation or a steam-treatment, or a combination of distillation and a steam-treatment.

The steam-treatment means blowing steam to a reaction composition to distil off the raw material alcohol together with the stream outside the system.

The distillation may be conducted under normal pressure or reduced pressure, but generally distillation under reduced pressure is more effective and can reduce the cost incurred by equipments.

Distillation conditions are as follows:
Temperature: 80 to 200° C., preferably 80 to 150° C.
Pressure: not more than 27 kPa (200 torr), preferably not more than 6 kPa (45 torr).
Amount of steam: 0 to 50 parts by weight relative to 100 parts by weight of a reaction composition.

The content of the raw material alcohol in the resulting component (A) is not more than 3000 ppm in view of decreasing an odor, preferably not more than 2000 ppm, more preferably not more than 1500 ppm, even more preferably not more than 1000 ppm, far more preferably not more than 500 ppm.

EXAMPLE

Preparation Example 1

In an autoclave were charged 1615.0 g (12.35 moles) of 1-octanol (Kalcol 0898, a product of Kao Corporation) and 6.9 g (0.12 mole) of potassium hydroxide, and after dehydration at 110° C., 13.3 kPa, an addition reaction was conducted while injecting thereinto 1434 g (24.69 moles) of propylene oxide with a pressure of 0.3 MPa at 120° C.

After completion of the reaction, aging was effected at the same reaction temperature for 6 hours, and then the reaction composition was allowed to cool to 80° C.

As a post-treatment, the resulting reaction composition was incorporated with 55 g of a synthetic absorbent (Kyoword 600S, Kyowa Chemical Industry, Co., Ltd.) to treat it for 1 hour at 4.0 kPa, and then the catalyst was removed by filtration. The content of 1-octanol in the resulting filtrate was 9000 ppm as determined by gas chromatography.

Then, 1000 g of the resulting filtrate was subjected to distillation under the conditions of 130° C. and 1.3 kPa to distil off 1-octanol. Further, a steam treatment by blowing 100 g of steam was conducted under the conditions of 145° C., 6.0 kPa for 5 hours.

The content of 1-octanol in the resulting product (alkyleneglycol ether 1 shown in Table 1) was determined by gas chromatography.

Preparation Example 2

Similarly to preparation example 1, alkyleneglycol ethers 2 through 12 shown in Table 1 (invention product) and Table 2 (comparative product) were prepared. Alkyleneglycol ethers 2 through 5 were subjected to purification similarly to preparation example 1, while alkyleneglycol ethers 6 through 12 were subjected only up to the removal of the catalyst by filtration and not subjected to the purification by distillation. The content of the raw material alcohol in each of the resulting alkyleneglycol ethers was determined by gas chromatography.

TABLE 1

| | General formula (1) | | | | |
|---|---|---|---|---|---|
| | $R^1$** | $R^2$ | n | m | Raw material(ppm) n = m = 0 |
| Alkyleneglycol ether 1 | C8 | H | 2.4 | 0 | 400 |
| Alkyleneglycol ether 2 | C8 | H | 1.6 | 0 | 1500 |
| Alkyleneglycol ether 3 | C8/C10 (molar ratio: 1/1) | H | 3.0 | 0 | 900 |
| Alkyleneglycol ether 4* | C8 | H | 2 | 0.5 | 500 |
| Alkyleneglycol ether 13 | C8 | H | 2.7 | 0 | 400 |

*in the $(PO)_n/(EO)_m$, $(PO)_n$ and $(EO)_m$ are arranged in block in this order relative to $R^1$.
**C8: n-octyl, C10: n-decyl

TABLE 2

| | General formula (1) | | | | |
|---|---|---|---|---|---|
| | $R^1$** | $R^2$ | n | m | Raw material(ppm) n = m = 0 |
| Alkykeneglycol ether 5 | C12 | H | 2.4 | 0 | 400 |
| Alkyleneglycol ether 6 | C8 | H | 2.4 | 0 | 26000 |
| Alkyleneglycol ether 7 | C8 | H | 0 | 2 | 30000 |
| Alkyleneglycol ether 8 | C8/C18 (molar ratio: 1/1) | H | 0 | 9 | 5000 |
| Alkyleneglycol ether 9 | C8 | H | 0 | 3 | 190000 |
| Alkyleneglycol ether 10 | C12 | H | 0 | 6 | 50000 |
| Alkyleneglycol ether 11 | 2-ethylhexyl | H | 0 | 4 | 150000 |
| Alkyleneglycol ether 12* | | | | | 2500 |

*$R-O-(C_2H_4O)_p-[(C_2H_4O)_q/(AO)_r]-H$ $[(C_2H_4O)_q/(AO)_r]$ is randomly arranged. R = isodecanol, p = 4, q = 1.5, AO = PO, r = 1.5
**C8: n-octyl, C12: n-dodecyl, C18: n-octadecyl Example 1

Using any of alkyleneglycol ethers 1-12 shown in Tables 1 and 2, and a surfactant, a detergent composition was prepared according to a conventional method, and the viscosity, foaming property and odor thereof were evaluated according to the following methods.

Conditions for measuring a viscosity are as follows. The results thereof are shown in Tables 3 and 4.

(1) Viscosity Measurement

Viscometer used: B-type viscometer (manufactured by Tokyo Keiki)

Rotor No./number of revolution: No. 1/12 rpm,

Measuring time: 1 minute

Temperature 30° C.: measured after a glass bottle containing a sample is immersed in a constant-temperature bath kept at 30° C.±1 for 1 hour.

(2) Foaming Test and Odor Test 1 ml of each of the detergent compositions shown in Tables 3 and 4 was dropped on a palm, hands and arms were washed, and a foaming property and an odor were evaluated by ten expert panellists according to the following evaluation criteria:

(Foaming Property)

4: it was felt that a foaming property was very good.

3: it was felt that a foaming property was good.

2: it was felt that a foaming property was moderate.

1: it was felt that a foaming property was not good.

An average of the ratings by the ten panellists was calculated and was assigned the following symbols: not less than 3.6: A, between 2.6 and 3.5: B, between 1.6 and 2.5: C, not more than 1.5: D.

(Odor)

4: an odor was not recognized at all.

3: a slight odor was recognized.

2: an odor was recognized.

1: a strong odor was recognized.

An average of the ratings by the ten panellists was calculated and was assigned the following symbols: not less than 3.6: A, between 2.6 and 3.5: B, between 1.6 and 2.5: C, not more than 1.5: D.

(3) Sebum-resistance Test

To 15 g (20 cm) of hair of a Japanese woman were applied 15 g of tap water and 0.1 mL of lanoline (manufactured by Yamakei Sangyo Co., Ltd.) used as a stain component. 1 mL of any of the surfactant compositions shown in Tables 3 and 4 was applied to the resulting hair and foamed for 30 seconds. The resulting foam was placed in a graduated cylinder of 5 cm in diameter and the amount of foam (mL) was measured.

TABLE 3

| Component | Detergent composition (wt. %) | Invention product | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| (A) | Alkyleneglycol ether 1 | 1.0 | | | | 1.0 | 1.0 | 1.0 | 2.0 | 2.0 | 2.0 | 2.0 | 1.0 | | | | |
| | Alkyleneglycol ether 2 | | 1.0 | | | | | | | | | | | 1.0 | | | |
| | Alkyleneglycol ether 3 | | | 1.0 | | | | | | | | | | | | | |
| | Alkyleneglycol ether 4 | | | | 1.0 | | | | | | | | | | | | |
| | Alkyleneglycol ether 13 | | | | | | | | | | | | | | 2.0 | 1.0 | 1.0 |
| | Alkyleneglycol ether 5 | | | | | | | | | | | | | | | | |
| | Alkyleneglycol ether 6 | | | | | | | | | | | | | | | | |

TABLE 3-continued

| Component | Detergent composition (wt. %) | Invention product | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| | Alkyleneglycol ether 7 | | | | | | | | | | | | | | | | |
| | Alkyleneglycol ether 8 | | | | | | | | | | | | | | | | |
| | Alkyleneglycol ether 9 | | | | | | | | | | | | | | | | |
| | Alkyleneglycol ether 10 | | | | | | | | | | | | | | | | |
| | Alkyleneglycol ether 11 | | | | | | | | | | | | | | | | |
| | Alkyleneglycol ether 12 | | | | | | | | | | | | | | | | |
| (B) | Laurylhydroxy sulfobetaine | | | | | | | | | | | | 1.0 | 1.0 | | | 1.0 |
| | Polyoxyethylene ($EO_p = 1$) alkyl ether ammonium sulphate | 19.0 | 19.0 | 19.0 | 19.0 | | | 19.0 | | | | | | | | | |
| | Polyoxyethylene ($EO_p = 1$) alkyl ether sodium sulphate | | | | | | | | | | | | 18.0 | 18.0 | 18.0 | 18.0 | 18.0 |
| | Coconut fatty acid amidopropylbetaine | | | | | | | | | | | | | | | 1.0 | |
| | Potassium laurate* | | | | | 19.0 | | | | | | | | | | | |
| | Lauryl phosphate K salt | | | | | | | | 18 | | | | | | | | |
| | Lauryl phosphate K salt/dilauryl phosphate K salt (monolauryl comp./dilauryl comp. = 75/25) | | | | | | | | | 18.0 | | 4.0 | | | | | |
| | Polyoxyethylene(1)lauryl phosphate K salt/polyoxyethylene(1)dilauryl phosphate K salt** (monolauryl comp./dilauryl comp. = 80/20) | | | | | | | | | | 18.0 | 14.0 | | | | | |
| | Alkyl polyglucoside*** | | | | | | 19.0 | | | | | | | | | | |
| | N-lauroylaminopropyl-N,N'-dimethyl amine oxide | | | | | | | 6.0 | | | | | | | | | |
| | p-Toluenesulfonate Na salt | | | | | | | 3.3 | | | | | | | | | |
| | Ethanol | | | | | | | 2.8 | | | | | | | | | |
| | Propyleneglycol | | | | | | | 3.5 | | | | | | | | | |
| | pH adjusting agent | q.s | q.s | q.s | q.s | q.s | q.s | q.s | q.s | q.s | q.s | q.s | q.s | q.s | q.s | q.s | q.s |
| | Purified water | Bal | Bal | Bal | Bal | Bal | Bal | Bal | Bal | Bal | Bal | Bal | Bal | Bal | Bal | Bal | Bal |
| pH(20-fold dilution: 25° C.) | | 6.5 | 6.0 | 6.2 | 7.2 | 6.8 | 5.8 | 6.7 | 8.0 | 7.5 | 5.5 | 6.0 | 6.5 | 6.5 | 7.1 | 6.8 | 6.8 |
| Evaluation Result | Foamig property | B | A | B | A | B | A | A | B | B | B | B | A | A | A | A | A |
| | Sebum resistance | 130 | 140 | 130 | 120 | — | — | — | — | — | — | — | 180 | 190 | 140 | 140 | 170 |
| | Viscosity | 200 | 400 | 360 | 250 | 250 | 180 | 420 | 400 | 500 | 300 | 350 | 300 | 400 | 150 | 150 | 100 |
| | Odor | A | B | B | A | A | A | A | A | A | A | A | A | B | A | A | A |

*PRIOLY B-100 (a product of Kao Corporation)
**the number in the parenthesis denotes an average added molar number of ethylene oxide
***MYDOL 10(a product of Kao Corporation)

TABLE 4

| Component | Detergent composition (wt. %) | Comparative product | | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 | 13 |
| (A) | Alkyleneglycol ether 1 | | | | | | | | | | | | | |
| | Alkyleneglycol ether 2 | | | | | | | | | | | | | |
| | Alkyleneglycol ether 3 | | | | | | | | | | | | | |
| | Alkyleneglycol ether 4 | | | | | | | | | | | | | |
| | Alkyleneglycol ether 13 | | | | | | | | | | | | | |

TABLE 4-continued

| | Detergent composition | Comparative product | | | | | | | | | | | | |
|---|---|---|---|---|---|---|---|---|---|---|---|---|---|---|
| Component | (wt. %) | 1 | 2 | 3 | 4 | 5 | 6 | 7 | 8 | 9 | 10 | 11 | 12 | 13 |
| (B) | Alkyleneglycol ether 5 | | 1.0 | | | | | | | | 2.0 | | | 1.0 |
| | Alkyleneglycol ether 6 | | | 1.0 | | | | | | | | | | |
| | Alkyleneglycol ether 7 | | | | 1.0 | | | | | | | | | |
| | Alkyleneglycol ether 8 | | | | | 1.0 | | | | | | 2.0 | | |
| | Alkyleneglycol ether 9 | | | | | | 1.0 | | | | | | | |
| | Alkyleneglycol ether 10 | | | | | | | 1.0 | | | | | | |
| | Alkyleneglycol ether 11 | | | | | | | | 1.0 | | | | | |
| | Alkyleneglycol ether 12 | | | | | | | | | 1.0 | | | | |
| | Laurylhydroxy sulfobetaine | | | | | | | | | | | | 1.0 | 1.0 |
| | Polyoxyethylene($EO_p = 1$) alkyl ether ammonium sulphate | 19.0 | 19.0 | 19.0 | 19.0 | 19.0 | 19.0 | 19.0 | 19.0 | 19.0 | | | | |
| | Polyoxyethylene($EO_p = 1$) alkyl ether sodium sulphate | | | | | | | | | | | | 19.0 | 19.0 |
| | Coconut fatty acid amido propylbetaine | | | | | | | | | | | | | |
| | Potassium laurate* | | | | | | | | | | | | | |
| | Lauryl phosphate K salt | | | | | | | | | | 18.0 | | | |
| | Lauryl phosphate K salt/Dilauryl phosphate K salt (monolauryl comp./dilauryl comp. = 75/25) | | | | | | | | | | | 18.0 | | |
| | Polyoxyethylene(1)lauryl phosphate K salt/polyoxyethylene(1)dilauryl phosphate K salt** (monolauryl comp./dilauryl comp. = 80/20) | | | | | | | | | | | | | |
| | Alkyl polyglucoside*** | | | | | | | | | | | | | |
| | N-lauroylaminopropyl-N,N'-dimethyl amine oxide | | | | | | 6.0 | | | | | | | |
| | p-Toluenesulfonate Na salt | | | | | | 3.3 | | | | | | | |
| | Ethanol | | | | | | 2.8 | | | | | | | |
| | Propylene glycol | | | | | | 3.5 | | | | | | | |
| | pH adjusting agent | q.s | q.s | q.s | q.s | q.s | q.s | q.s | q.s | q.s | q.s | q.s | q.s | q.s |
| | Purified water | Bal | Bal | Bal | Bal | Bal | Bal | Bal | Bal | Bal | Bal | Bal | Bal | Bal |
| pH(20-fold dilution: 25° C.) | | 6.5 | 6.5 | 6.5 | 6.5 | 6.5 | 6.5 | 6.7 | 6.5 | 6.5 | 8.0 | 7.5 | 6.8 | 6.8 |
| Evaluation Result | Foamig property | D | D | B | B | D | C | B | C | D | D | D | D | C |
| | Sebum resistance | 70 | 80 | 130 | 120 | — | — | — | — | — | — | — | 90 | 100 |
| | Viscosity | 20 | 190 | 220 | 300 | 500 | 200 | 400 | 110 | 80 | 350 | 500 | 50 | 200 |
| | Odor | A | A | D | D | C | D | D | D | B | A | C | A | A |

*PRIOLY B-100 (a product of Kao Corporation)
**the number in the parenthesis denotes an average added molar number of ethylene oxide
***MYDOL 10(a product of Kao Corporation)

Example 2

A hair shampoo having the following composition was prepared:

| (Component) | (% by weight) |
|---|---|
| Alkyleneglycol ether 1 | 2.0 |
| Polyoxyethylene (2) lauryl ether sodium sulphate* | 15.0 |
| Lauric acid diethanol amide | 2.0 |
| Cationic polymer** | 0.2 |
| Silicone*** | 1.0 |
| Flavour, Methyl paraben | q.s. |
| Purified water | Balance |
| Total | 100 |

*the number in the parenthesis denotes an average added molar number of ethylene oxide
**POIZ C-150L; a product of Kao Corporation
***Silicone BY22-060; a product of Dow Corning Toray This hair shampoo had a favorable foaming property, no odor and an adequate viscosity (2000 mPa·s).

Example 3

A body shampoo having the following composition was prepared:

| (Component) | (% by weight) |
|---|---|
| Alkyleneglycol ether 2 | 0.8 |
| Laurate salt* | 30.0 |
| Amidopropylbetaine** | 2.0 |
| Glycerine | 3.0 |
| Flavour, Methyl paraben | q.s. |
| Purified water | Balance |
| Total | 100 |

*PRIOLY B-100; a product of Kao Corporation
**AMPHITOL 20AB; a product of Kao Corporation This body shampoo had a favorable foaming property, no odor and an adequate viscosity (500 mPa·s).

Example 4

A face wash having the following composition was prepared:

| (Component) | (% by weight) |
| --- | --- |
| Alkyleneglycol ether 1 | 1.0 |
| Lauryl phosphate K salt | 10.0 |
| Laurate K salt | 10.0 |
| Myristate K salt | 8.0 |
| Palmitate K salt | 8.0 |
| Sorbitol | 10.0 |
| Flavour, Methyl paraben | q.s. |
| Purified water | Balance |
| Total | 100 |

This face wash had a favorable foaming property, no odor and an adequate viscosity (50000 mPa·s).

Example 5

A face wash having the following composition was prepared:

| (Component) | (% by weight) |
| --- | --- |
| Alkyleneglycol ether 1 | 1.0 |
| Lauryl phosphate K salt | 2.0 |
| Polyoxyethylene(1)lauryl phosphate K salt | 5.0 |
| Polyoxyethylene(1)lauryl ether sodium sulphate* | 10.0 |
| Lauryl hydroxylsulfobetaine** | 3.0 |
| Alkyl acrylate-methacrylate copolymer*** | 0.5 |
| Ethyleneglycol distearate | 2.0 |
| Na$_2$SO$_4$ | 3.0 |
| Flavour, Methyl paraben | q.s. |
| Purified water | Balance |
| Total | 100 |

*the number in the parenthesis denotes an average added molar number of ethylene oxide
**AMPHITOL 20HD; a product of Kao Corporation
***Carbopol ETD2020; a product of B F Goodrich Corporation This face wash had a favorable foaming property, no odor and an adequate viscosity (30000 mPa·s).

Example 6

A hair shampoo having the following composition was prepared:

| (Component) | (% by weight) |
| --- | --- |
| Alkyleneglycol ether 13 | 0.6 |
| Polyoxyethylene(1)lauryl ether sodium sulphate* | 13.8 |
| Coconut fatty acid amidopropylbetaine | 1.2 |
| Lauryl hydroxylsulfobetaine | 0.6 |
| Cationic polymer** | 0.2 |
| Silicone*** | 2.0 |
| Ethyleneglycol distearyl ether | 0.5 |
| Flavour, Methyl paraben | q.s. |
| Purified water | Balance |
| Total | 100 |

*the number in the parenthesis denotes an average added molar number of ethylene oxide
**Jaguar C-13C; a product of Rhodia Company
***Silicone BY22-060; a product of Dow Corning Toray This hair shampoo had a favorable foaming property and a favorable sebum resistance, no odor and an adequate viscosity (3000 mPa·s).

Example 7

A hair shampoo having the following composition was prepared:

| (Component) | (% by weight) |
| --- | --- |
| Alkyleneglycol ether 13 | 0.8 |
| Lauryl ether sodium sulphate | 8.0 |
| Polyoxyethylene(3)lauryl ether sodium sulphate* | 8.0 |
| Coconut fatty acid monoethanol amide** | 0.6 |
| Lauryl hydroxylsulfobetaine | 0.5 |
| Cationic polymer*** | 0.2 |
| Silicone**** | 2.0 |
| Ethyleneglycol distearyl ether | 1.5 |
| Flavour, Methyl paraben | q.s. |
| Purified water | Balance |
| Total | 100 |

*the number in the parenthesis denotes an average added molar number of ethylene oxide
**AMINON C-01S; a product of Kao Chemical Corporation Shanghai
***Polymer JR-400; a product of Dow Chemical Company
****Silicone BY22-007; a product of Dow Corning Toray This hair shampoo had a favorable foaming property and a favourable sebum resistance, no odor and an adequate viscosity (6000 mPa·s).

The invention claimed is:

1. A thickening/foam-promoting agent comprising the following component (A):

(A) a compound represented by the following formula (1):

$$R^1O-(PO)_n/(EO)_m-R^2 \quad (1),$$

wherein $R^1$ is a linear alkyl or an alkenyl group having 8 to 10 carbon atoms, PO is a propyleneoxy group, EO is an ethyleneoxy group, an average added molar number n is a number of 1.5 to 3.0, an average added molar number m is a number of 0 to 0.5, and $R^2$ is a hydrogen atom or a methyl group, wherein a content of an alcohol of the formula (1), when n=0, m=0 and $R^2$ is a hydrogen atom, is not more than 3000 ppm.

2. The thickening/foam-promoting agent according to claim 1, wherein the content of the alcohol of the formula (1), when n=0, m=0 and $R^2$ is a hydrogen atom, is not more than 1500 ppm.

3. The thickening/foam-promoting agent according to claim 1 or 2, which is used for a detergent composition applied to skin or hair.

4. A detergent composition comprising the following components (A) and (B):

(A) a compound represented by the following formula (1):

$$R^1O-(PO)_n/(EO)_m-R^2 \quad (1),$$

wherein $R^1$ is a linear alkyl or an alkenyl group having 8 to 10 carbon atoms, PO is a propyleneoxy group, EO is an ethyleneoxy group, an average added molar number n is a number of 1.5 to 3.0, an average added molar number m is a number of 0 to 0.5, and $R^2$ is a hydrogen atom or a methyl group, wherein a content of an alcohol of the formula (1), when n=0, m=0 and $R^2$ is a hydrogen atom, is not more than 3000 ppm, and (B) a surfactant other than the component (A),
wherein the detergent composition is applied to skin or hair.

5. The detergent composition according to claim 4, wherein the component (B) is composed of at least two kinds of surfactants, and one of the surfactants is a sulfobetaine.

6. The detergent composition according to claim 4, wherein the content of the alcohol of the formula (1), when n=0, m=0 and $R^2$ is a hydrogen atom, is not more than 1500 ppm.

7. The detergent composition according to claim 4 or 5, wherein the component (A) is contained in an amount of 0.1 to 20% by weight.

8. A process for producing the component (A) according to claim 1 in which a content of a raw material alcohol is reduced to not more than 3000 ppm, the process comprising:
reacting the raw material alcohol represented by the formula (2):
$R^1$ OH (2),
Wherein $R^1$ is a linear alkyl or an alkenyl group having 8 to 10 carbon atoms,
with propylene oxide and/or ethylene oxide, and
then distilling away the raw material alcohol.

9. A method for thickening/foam-promoting a detergent composition, comprising adding to the detergent composition the following component (A):
(A) a compound represented by the following formula (1):

$$R^1O-(PO)_n/(EO)_m-R^2 \qquad (1),$$

wherein $R^1$ is a linear alkyl or an alkenyl group having 8 to 10 carbon atoms, PO is a propyleneoxy group, EO is an ethyleneoxy group, an average added molar number n is a number of 1.5 to 3.0, an average added molar number m is a number of 0 to 0.5, and $R^2$ is a hydrogen atom or a methyl group,
wherein a content of an alcohol of the formula (1), when n=0, m=0 and $R^2$ is a hydrogen atom, is not more than 3000 ppm,
wherein the detergent composition comprises a surfactant other than the component (A).

10. The method according to claim 9, wherein the content of the alcohol of the formula (1), when n=0, m=0 and $R^2$ is a hydrogen atom, is not more than 1500 ppm.

11. The method according to claim 9, wherein the detergent composition is applied to skin or hair.

* * * * *